(12) United States Patent
Chun et al.

(10) Patent No.: US 10,888,442 B2
(45) Date of Patent: Jan. 12, 2021

(54) SUPER ELASTIC, BIOABSORBABLE ENDOVASCULAR DEVICES

(71) Applicant: UNIVERSITY OF PITTSBURGH—OF THE COMMONWEALTH SYSTEM OF HIGHER EDUCATION, Pittsburgh, PA (US)

(72) Inventors: Youngjae Chun, Pittsburgh, PA (US); William R. Wagner, Gibsonia, PA (US); Xinzhu Gu, Pittsburgh, PA (US); Peter Drew Wearden, Pittsburgh, PA (US); Tomo Yoshizumi, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 270 days.

(21) Appl. No.: 15/525,411

(22) PCT Filed: Nov. 11, 2015

(86) PCT No.: PCT/US2015/060064
§ 371 (c)(1),
(2) Date: May 9, 2017

(87) PCT Pub. No.: WO2016/077410
PCT Pub. Date: May 19, 2016

(65) Prior Publication Data
US 2017/0340463 A1    Nov. 30, 2017

Related U.S. Application Data

(60) Provisional application No. 62/078,023, filed on Nov. 11, 2014.

(51) Int. Cl.
*A61F 2/86* (2013.01)
*A61L 31/14* (2006.01)
(Continued)

(52) U.S. Cl.
CPC ............. *A61F 2/86* (2013.01); *A61F 2/07* (2013.01); *A61F 2/82* (2013.01); *A61L 31/022* (2013.01);
(Continued)

(58) Field of Classification Search
CPC ...... A61F 2/04; A61F 2/07; A61F 2/82; A61F 2/86; A61F 2210/0004; A61F 2210/0014; A61L 31/148; A61L 2400/16
See application file for complete search history.

(56) References Cited

U.S. PATENT DOCUMENTS 7,824,601 B1 * 11/2010 Stankus ................ A61L 31/14
264/131
7,862,607 B2    1/2011 McDermott et al.
(Continued)

OTHER PUBLICATIONS

International Search Report dated Feb. 18, 2016 (ISA/KR).

*Primary Examiner* — Dinah Baria
(74) *Attorney, Agent, or Firm* — Eckert Seamans Cherin & Mellott; Carol A. Marmo (57) ABSTRACT

The invention relates to endovascular medical implant devices and materials of composition for forming these devices to provide improved mechanical properties and biodegradability. The devices include a combination or integration of superelastic material, biodegradable metal and, thin film nitinol and/or biodegradable polymer. A structural frame is formed of individual elongated pieces composed of biodegradable metal. These pieces are joined together by connector pieces composed of superelastic material. At least a portion of the structural frame has deposited thereon the thin film nitinol and/or biodegradable polymer.

(Continued)

The structural frame of the device is collapsible for insertion in a delivery tube and, recoverable for deployment and placement in a vascular location of a patient body.

8 Claims, 7 Drawing Sheets

(51) Int. Cl.
  *A61L 31/02* (2006.01)
  *A61L 31/08* (2006.01)
  *A61L 31/18* (2006.01)
  *A61F 2/82* (2013.01)
  *C08L 67/04* (2006.01)
  *C08L 75/04* (2006.01)
  *A61F 2/07* (2013.01)

(52) U.S. Cl.
  CPC ............ *A61L 31/088* (2013.01); *A61L 31/14* (2013.01); *A61L 31/148* (2013.01); *A61L 31/18* (2013.01); *C08L 67/04* (2013.01); *C08L 75/04* (2013.01); *A61F 2210/0004* (2013.01); *A61F 2210/0014* (2013.01); *A61F 2250/0018* (2013.01); *A61F 2250/0026* (2013.01)

(56) References Cited

U.S. PATENT DOCUMENTS

| | | | |
|---|---|---|---|
| 8,435,281 B2 | 5/2013 | Weber | |
| 8,834,902 B2 | 9/2014 | Mangiardi | |
| 2002/0183826 A1* | 12/2002 | Dorn | A61F 2/958 623/1.11 |
| 2006/0051394 A1 | 3/2006 | Moore et al. | |
| 2007/0156232 A1* | 7/2007 | Kutryk | A61L 27/08 623/1.41 |
| 2008/0033522 A1 | 2/2008 | Grewe et al. | |
| 2013/0204349 A1* | 8/2013 | Hansen | A61F 2/07 623/1.16 |

* cited by examiner

SUPER ELASTIC, BIOABSORBABLE ENDOVASCULAR DEVICES

CROSS REFERENCE TO RELATED PATENT APPLICATION

This patent application claims the benefit of U.S. Provisional Patent Application No. 62/078,023, entitled "Super Elastic, Bioabsorbable Endovascular Devices", filed on Nov. 11, 2014, the contents of which are incorporated herein by reference.

FIELD OF THE INVENTION

The invention relates to super elastic, bioabsorbable endovascular devices and materials of composition for these devices to provide improved mechanical properties and biodegradability for implanting the devices in a patient.

BACKGROUND

The introduction of minimally invasive surgical techniques and the development of various endovascular devices have substantially improved human health care over several decades. Further improvements may be realized by increasing the functionality of these devices and extending the types of procedures where such devices may be employed.

It is believed that improvement in the materials of composition and construction of the endovascular devices will provide increased opportunities for optimizing the benefits derived from the devices. For example, it is desired to utilize different materials to achieve both improved mechanical properties and biodegradability for medial implant devices. The use of degradable components allows a tissue engineering approach to be pursued where no permanent foreign body is left behind in the patient when there is no longer a need for the implanted medical device. Devices or pieces of devices remaining in the patient can potentially pose a risk of infection, fibrosis or abrasion. Constructing devices from biodegradable materials can substantially reduce or eliminate these risks.

There are many known medical conditions and diseases wherein treatment can be improved by the development of improved materials for implantable medical devices, including the following examples.

Pediatric Heart Valve Replacement Methods and Shortcomings

Heart valve disease is a condition in which the valve, which is positioned between the main pumping chamber of the heart (left ventricle) and the main artery to the body (aorta), malfunctions. Heart valve disease may be a congenital condition. For infants, defects in cardiac valves and associated structures account for 25 to 30 percent of all cardiovascular malformations. In adults, valvular heart disease remains a major cause of morbidity and mortality. For example, approximately 98,000 valve replacements were performed in the United States in 2006.

There are typically two types of prosthetic heart valves for replacement, which are mechanical and bioprosthetic. Mechanical heart valves are made entirely of synthetic materials such as metals and polymers, while bioprosthetic heart valves are made of tissue from animal (e.g., bovine or porcine) or humans. Mechanical heart valves are very durable, most lasting at least 20 to 30 years. However, these valves have limited central flow due to their designs such as bileaflets, the ball in cage, or tilting disc. In addition, one of the major drawbacks is that mechanical heart valves require daily anticoagulant treatment because of an increased risk of artificial material induced thrombosis and thromboembolism.

Bioprosthetic heart valves have improved central blood flow due to their bio-mimicking trileaflet design and do not require anticoagulant therapy. However, these bioprosthetic heart valves also have associated disadvantages, which include limited durability due to leaflet calcification, leaflet tearing, fatigue damage, and tissue failure. Therefore, it has been found that about 10 to 20 percent of homograft bioprostheses and 30 percent of heterograft bioprostheses fail within 10 to 15 years of implantation, and require replacement.

In the pediatric population, in particular, failure of the mechanical and biological valve replacement to grow, regenerate and remodel require multiple subsequent reoperations to place larger devices to accommodate somatic growth. A tissue-engineered heart valve has been an elegant alternative to overcome the above-mentioned limitations.

The scaffolds utilized in heart valve tissue engineering include decellularized xenografts/homografts and synthetic polymeric scaffolds. Depleted of cells and cellular components, xenografts/homografts possess micro-structure, mechanical properties and physiological hemodynamics similar to their native counterparts. Further, signaling molecules existing in the scaffolds provide natural cues to guide cell adhesion and growth, and tissue formation and remodeling. Successful recellularization has been demonstrated in animal models using decellularized matrices. However, a significant concern is the severe immunogenic response, which leads to early graft failure. In addition, it is controversial to implant xenografts in humans and, the use of homografts may raise ethical concerns and limited donors are problematic. Therefore, the utilization of synthetic polymeric scaffold alone is quite attractive, since the depletion of biological component can greatly reduce the potential immunogenic response and the material source is much more abundant and the handling is easier.

The main challenge of the synthetic scaffold is to recruit autologous cells, which have to differentiate into the appropriate phenotype to achieve tissue remodeling and heart valve functionality. Insufficient cellularization on a plain scaffold may result in thrombus formation and calcification, and eventually lead to leaflet stiffening and tearing. Combining the synthetic scaffolds with collagen, cells, or ECM gel has demonstrated good cellular infiltration and tissue integration in both the animal and clinical studies.

Furthermore, both mechanical and bioprosthetic heart valves require an open heart surgery, which has a severe risk factor for infants and young children who are too weak or ill to undergo major open surgery. A less invasive therapy, i.e., percutaneous heart valve replacement, has drastically improved with the development of novel biomaterials and suggests innovative treatment strategies. There are known in the art the following three percutaneous heart valve (PHV) aortic valve devices:

(i) The Edwards "SAPIEN" Transcatheter Heart Valve (THV) is made of cow tissue attached to a stainless steel mesh frame with a polyester wrap, and it requires 22-24 Fr (~8 mm) catheter for delivery for 23~26 mm in diameter;

(ii) The Medtronic "CoreValve" is made of porcine pericardial valve sutured within a three-level self-expanding frame and, it is delivered via 18 Fr catheter for 20~29 mm in diameter and has been used to treat inoperable aortic stenosis;

(iii) The Medtronic "Melody" pulmonary valve is made of natural venous tissue with metallic stent and, it is delivered via 22 Fr catheter for larger than 16 mm in diameter and is used to treat pulmonary valve replacement for both pediatric and adult patents.

While percutaneous heart valve replacement is an emerging technology with a few commercially available devices, these known devices require very bulky catheters due to the materials used in the valves (e.g., bovine, porcine or human tissues), which may not be suitable for pediatric patients. Not only are these valves not "off-the-shelf" products that retain their ideal strength and properties during long-term storage and function successfully after replacement, but the valves will also not grow with the growth of a child.

Ventricular Septal Defects

Congenital cardiac malformations are the most common form of congenital diseases, afflicting ~1% of all live births. Congenital intracardiac shunts are very common in children with congenital heart disease (CHD), ventricular septal defects of some form occur in ~50% of patients with CHD. Such lesions often lead to shunting of blood to the low resistance pulmonary circulation. Infants without pulmonary stenosis often suffer from increased pulmonary blood flow and congestive heart failure. Surgical banding of the pulmonary artery is a palliative procedure meant to decrease pulmonary blood flow and pulmonary artery pressure, thereby "protecting" the lungs against development of elevated vascular resistance and reducing the volume overload to the systemic ventricle. In the current era, pulmonary artery banding is carried out in infants with large non-restrictive ventricular septal defects and in univentricular physiology is when partial or total routing of systemic venous return to the pulmonary circulation is not advisable. The banding is typically performed in the first few weeks to months of life and followed eventually by surgical repair (e.g. closure of the ventricular septal defect). Banding continues to require an invasive surgical approach including a midline sternotomy and occasionally needs to be done with the use of cardiopulmonary bypass. Despite advances in surgical techniques, significant rates of morbidity and mortality remain. The disruption in children's lives, and the interruptions in their socialization and development in their homes and communities are also significant.

Moreover, in patients that do not go on to early definitive surgical repair, the long-term durability of pulmonary artery bands has been questioned, and a gradual "loosening" of the band with resultant pulmonary hypertension can occur. Moreover, optimal intra-operative adjustment of the band tightness is challenging. Patients with inadequate bands at the time of definitive surgical repair have an increased risk of mortality. In the majority of patients that survive the banding operation there is significant morbidity associated with the post-operative recovery from open-chest pulmonary artery banding. Children have significant pain from the surgical incision, are required to stay in the intensive care unit (ICU) for many days, and often require prolonged ventilation. Consequently, they are vulnerable to a host of surgical complications including (but not limited to) bleeding, chylothorax, diaphragm paresis/paralysis, mediastinal infection, sepsis, pleural effusion and pneumothorax. Both the children requiring multiple/serial surgeries and their families are adversely affected by the prolonged rehabilitation from each surgery. Transcatheter or non-surgical pulmonary artery banding is now a reality. A transcatheter bulk nitinol flow restrictor has been developed by AGA Corp (Golden Valley, Minn.) and used in the clinical setting, however, this device is bulky, thrombogenic, becomes completely obstructive in a matter of months and therefore must be surgically removed within 6 weeks of implantation.

The development of a pulmonary artery band amenable to placement in even small children with transcatheter technology, rather than with surgery, would dramatically improve the recovery and rehabilitation of children following banding.

Coronary Artery Disease (CAD)

Coronary artery disease (CAD) is the most common type of heart disease and the leading cause of death worldwide. The disease is caused by plaques building up in the coronary arteries, which narrows the artery and prevents adequate blood supply to the myocardium. CAD was responsible for approximately 20% of all deaths in 2005 in the United States, according to the American Heart Association. Among the interventions to restore blood flow, angioplasty (removal or compression of the plaque by use of catheter, balloon or stent) and bypass grafting (detouring around the blockage) are mostly well established methods for treating CAD. In 2006, 652,000 patients in the US were treated using coronary intervention surgery with stent implantation with an approximately total cost of $31 billion.

Clinically applied bare metal stents (BMS) are usually made of non-degradable metallic materials, such as 316 stainless steel, Ta, cobalt-chromium alloy and titanium alloy. The initial clinical results of BMS are generally quite attractive, however re-narrowing of the treated artery is commonly observed in 20-30% of patients. This re-narrowing of the treated artery is due to restenosis, which results from excessive smooth muscle proliferation. Besides, acute occlusion by thrombosis presents another limitation in the application of BMS. Drug eluting stent (DES) has been developed by incorporating antiproliferative agents and markedly improved clinical outcomes by reducing the rate of restenosis. The sirolimus eluting Cypher stent using stainless steel and a biostable polymer coating (Cordis/J&J) received FDA approval in 2003. Afterwards, the paclitaxel eluting Taxus stent (Boston Scientific), the zotarolimus eluting Endeavor stent (Medtronic), and XIENCE V™ everolimus drug eluting stent (Abbott) were approved for clinical trials by the FDA.

Long term placement of a non-degradable stent, including the DES, could still cause discomfort and provide a source for thrombosis and fibrosis in patients. Also, it provides challenges for subsequent surgical or intravascular interventions. To address such limitations, biodegradable metallic stents have been developed with their potential to provide the necessary acute mechanical support, followed by degradation to avoid the complications associated with foreign body reactions. Magnesium alloys have engendered great interests as materials to produce bioabsorbable metallic stents in coronary arteries, with the benefit of less local inflammation, reduced platelet adhesion and less neo-intima formation than traditional non-biodegradable metallic stents. Good biocompatibility has been demonstrated in porcine coronary artery model. Clinical studies also showed feasibility, good safety profile, and promising angiographic performance.

Recently, new generation of stent systems, called covered stents have been developed. A thin membrane is used to cover the interior luminal or adluminal surface of the stents. Currently, most commercially available covering membranes are usually made of non-degradable ePTFE thin film. The thin membrane not only decreases the radial pressure of the stent, but also reduces the restenosis and re-embolization by acting as the barrier between the vessel wall and the blood stream. In addition, the thin membranes can serve as drug release reservoir.

Peripheral Arterial Disease (PAD)

Lower extremity peripheral arterial disease (PAD) represents a significant disease burden in the United States. Epidemiological studies have estimated the prevalence of PAD at between 3-10% with an increase to 10-15% in persons over 70 years. Industry wide estimates suggest that for femoral and popliteal disease alone, there will be an increase to 1.7 million procedures by 2020. Current treatment trends for PAD include an expanding role for endovascular procedures to revascularize ischemic limbs as compared to open bypass. Recently a randomized trial in patients with chronic limb ischemia revealed no difference in amputation free survival at one year between endovascular versus open bypass surgery. However, open surgical repair using vein graft remains the gold standard of treating complex lesions in the extremities due to better long term patency (i.e. reduced thrombogenicity). Therefore, a critical need exists for developing endovascular technology to treat PAD that is non-thrombogenic or at least comparable to vein grafts.

Two common approaches currently used to treat PAD include bypass using autologous vein grafts and endovascular placement of polymer coated stents. While autologous vein grafts remain patent longer than expanded polytetrafluoroethylene (ePTFE) grafts (5 year patency of 74-76% versus 39-52% for above the knee femoral popliteal bypass), there are still significant thrombotic complications. These thrombotic complications represent the key problem in the continued treatment and management of PAD. Approximately one third of patients in both groups developed thrombosis requiring re-intervention with attempts at mechanical thrombectomy and/or bypass grafting. Therefore, graft thrombosis is significant and represents the major obstacle in treating PAD. Furthermore, the cost increases by a factor of 2 to 4 times when the initial treatment plan fails regardless of the approach used. Therefore, any technology that ameliorates or prevents endograft thrombus development will have a significant impact on patient quality of life and functional status not to mention a profound impact on decreasing the amount of health care dollars spent on PAD.

Excessive Hemorrhage

There is an immediate need for developing advanced catheter-based devices to prevent excessive hemorrhage in wounded soldiers at triage locations near the battlefield. Therefore, the invention provides both an ultra-low profile catheter-based vascular occluder for percutaneous treatment of massive hemorrhage and also covered stents for later, definitive repair of vascular injuries.

It is currently estimated that extremity injury is the leading cause of preventable deaths on the battlefield, with estimates of up to 79% being preventable with adequate control of bleeding. The majority of these injuries require vascular repair that involve peripheral arteries (arms and legs). Rapid, minimal invasive control of bleeding prior to definitive repair would reduce mortality and morbidity in most of these cases. Therefore, there is an immediate need in battlefield situations for vascular injury control devices. In general, these devices should either prevent the bleeding by isolating the injury or provide a conduit for repair of the vascular system. New low profile concepts will have substantial military and civilian applications for the treatment of trauma, iatrogenic injury, aneurysmal disease and other internal vascular related conditions.

Thus, there is a need in the art to develop endovascular devices and materials that provide improved mechanical properties and biodegradability as implant devices for use in medical conditions and diseases such as, but not limited to, pediatric heart diseases, coronary artery disease, peripheral arterial disease and excessive hemorrhage.

SUMMARY OF THE INVENTION

In one aspect, the invention provides an endovascular medical implant device including a structural frame constructed of a plurality of elongated pieces composed of biodegradable metal and, one or more connectors composed of superelastic material and structured to join together the plurality of elongated pieces. The medical implant device further includes a deposition material selected from biodegradable polymer, thin film nitinol and, mixtures and combinations thereof, which is deposited on at least a portion of the structural frame.

The superelastic material can include nitinol. The biodegradable metal can be selected from the group consisting of magnesium, iron and, alloys and mixtures thereof. The biodegradable polymer can be selected from the group consisting of polyester, polyurethane urea, polycaprolactone, poly-L-lactic acid, polyglycolic acid and mixtures thereof. In certain embodiments, the biodegradable polymer is in a form selected from a membrane applied to a backbone of the structural frame and a coating deposited on the plurality of elongated pieces composed of biodegradable metal. The coating can include electrospun fibers formed by electrospinning.

The structural frame can be elastically deformable from an original form to a collapsed structure. The collapsed structure can be placed in a delivery tube, deployed from the delivery tube into a patient body and upon being deployed, the collapsed structure can recover to the original form. The delivery tube can be a catheter or other tube that mimics a blood vessel. In certain embodiments, the tube is composed of silicone.

The plurality of elongated pieces of the structural frame can be selected from the group consisting of wires, strips and, combinations and mixtures thereof.

In certain embodiments, the superelastic material is nitinol, the biodegradable metal is selected from magnesium, magnesium alloy, iron, iron alloy and mixtures thereof, and the deposition material is selected from thin film nitinol (not bioabsorbable), polyurethane urea membrane, and mixtures and combinations thereof. The nitinol can constitute about 10% or less by weight, the biodegradable metal can constitute about 80% or greater by weight, and the deposition material can constitute about 5% or less, or about 10% or less by weight, based on total weight of the device.

In another aspect, the invention provides a method of preparing an endovascular device. The method includes forming a structural frame by obtaining a plurality of elongated pieces composed of biodegradable metal, obtaining one or more connectors composed of superelastic material, and employing the one or more connectors to join together the plurality of elongated pieces to form the structural frame, and depositing a deposition material selected from thin film nitinol, biodegradable polymer and, mixtures and combinations thereof on at least a portion of the structural frame.

The depositing of the deposition material can include applying a biodegradable polymer membrane to a backbone of the structural frame, applying a nitinol thin film to a backbone of the structural frame, or depositing a biodegradable polymer coating on the plurality of elongated pieces composed of biodegradable metal. In certain embodiments, the coating is composed of polyurethane urea electrospun fibers.

The method can further include elastically collapsing the structural frame from an original form to a collapsed structure, inserting the collapsed structure in a delivery tube, deploying the collapsed structure from the delivery tube into a vascular target in a patient body, and recovering the original form of the structural frame in the vascular target.

The one or more connectors can be applied to the plurality of elongated pieces using a mechanism selected from the group consisting of mechanical clamping, gluing, suturing, and micro-laser welding.

The endovascular device can be integrated into a stent delivery catheter system.

BRIEF DESCRIPTION OF THE DRAWINGS

A full understanding of the disclosed concept can be gained from the following description of the preferred embodiments when read in conjunction with the accompanying drawings, in which.

DETAILED DESCRIPTION OF PREFERRED EMBODIMENTS

The invention relates to superelastic, bioabsorbable endovascular devices, biodegradable materials for their construction, methods for preparation and uses as medical implant devices.

A key aspect of this concept is the combination of small, highly elastic, non-degradable connection pieces, with structural elements and bioactive components made from degradable metals and polymers. The integration of more than one, e.g., two or three, implantable biomaterials together with novel manufacturing approaches can result in the formation of a variety of endovascular devices applicable to many life-threatening vascular diseases, with particular applications in the pediatric and geriatric populations. The devices are constructed and formed of a combination of materials selected from a superelastic material, e.g., a metal alloy, a biodegradable metal and a biodegradable polymer or a thin film nitinol.

In certain embodiments, the endovascular devices can include a skeletal structure, e.g., frame structure or framework, which is composed of biodegradable metal and superelastic material, that has a deposition material, such as, biodegradable polymer or thin film nitinol (not bioabsorbable), applied or deposited thereon. The biodegradable metal can be in the form of a plurality of individual elongated, e.g., straight, pieces or segments, such as wires, strips and combinations or mixtures thereof. The superelastic material can be in the form of connector pieces or segments, e.g., wires, struts or tubes, to integrate, join or connect together the individual biodegradable metal elongated pieces or segments. For example, one end of a first biodegradable metal piece or segment can be connected to an end of a second biodegradable metal piece or segment by use of a superelastic connector, e.g., tube and/or strut, positioned between these two ends. The superelastic connector can be applied to the biodegradable metal segment using a variety of mechanisms, such as, but not limited to, mechanical clamps, adhesive (e.g., glue), sutures (e.g., thread) and micro-laser welding.

Figure 1:
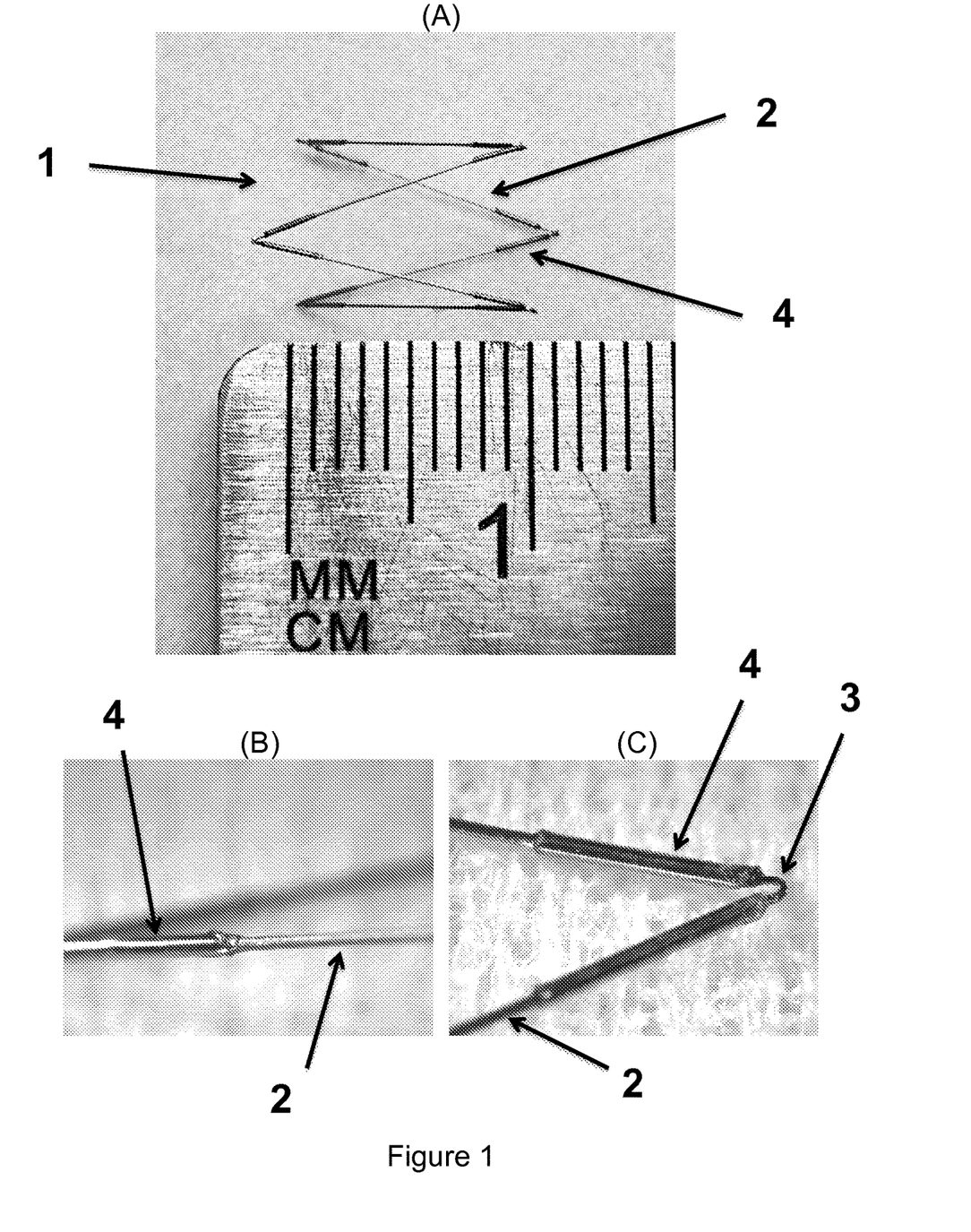
FIG. 1A is an image showing a stent frame structure composed of biodegradable metal wires integrated with superelastic material connector segments.
FIG. 1B is an image showing a detailed view of an integrated biodegradable metal wire and superelastic material connector (tube) as shown in FIG. 1A.
FIG. 1C is an image showing a detailed view of the superelastic material connector segment (tube and strut) as shown in FIG. 1A.

FIG. 1A shows a stent frame structure 1 constructed of a plurality of straight, biodegradable metal wires 2 integrated with superelastic material connector tubes 4. FIG. 1B shows a detailed view of one of the metal wires 2 integrated with one of the superelastic material tubes 4. FIG. 1C shows a detailed view of the metal wires 2 integrated with the superelastic material tubes 4, which are joined by a superelastic material (v-shaped) strut 3.

The metallic portion of the frame structure provides sufficient mechanical force with a low-profile design, maintains the geometry of the device structure, and is biocompatible. Additionally, in accordance with the invention, the elongated pieces or segments are composed of a biocompatible metal that is also biodegradable. Non-limiting examples of biodegradable metals for use in constructing and forming the metallic frame include, but are not limited to, magnesium, magnesium-based alloy, iron, iron-based alloy, and mixtures thereof. The biodegradable metal constitutes about 80% or greater or about 90% or greater of the total mass of the endovascular device.

Biodegradable materials such as magnesium, magnesium-based alloys, iron and iron-based alloys are attractive as alternatives for permanent metallic devices, because they can resorb through oxidation over a specific period of time. Magnesium alloys remain in the body only for as long as is needed for them to perform their specific functions (e.g., maintaining geometry of skeletal structures or exerting mechanical forces). Beyond the expected period of time for functioning, the magnesium alloys gradually degrade and finally disappear. This temporary existence can reduce or potentially eliminate the long-term complications or risk of medical implant devices, such as in-stent restenosis, infections, or mechanical instability in cases of pediatric patients. Magnesium shows biocompatibility and low thrombogenicity. Although, these biodegradable materials have potentially attractive long-term biocompatibility, there are significant limitations associated with these materials. Iron has a slow degradation profile and, as previously mentioned, magnesium does not possess sufficient mechanical properties (i.e., ductility) for endovascular devices.

The superelastic material for use in the invention includes a metal alloy, such as, but not limited to, nickel-titanium alloy (known as "nitinol"), which is used to form miniature connections within the endovascular device of the invention. The connections can be in the form of tubes or struts, e.g., v-shaped struts. Nitinol is a preferred metal alloy due to its shape memory property ("superelastic" property). The shape memory response is defined as a mechanical (elastic) deformation in a low temperature state (i.e., martensite) with deformations fully recovered when the material is heated to body temperature (i.e., austenite). This shape memory behavior of nitinol is critical for transcatheter devices because the metallic frame composed of nitinol can easily be collapsed into a small diameter catheter (or any tube that mimics a blood vessel) in its martensite phase. Upon an exposure to blood temperature, the collapsed nitinol metallic frame deploys spontaneously to its original shape (i.e., the austenite phase). Because the magnitude of recoverable elastic deformation of nitinol is much greater than elastic deformation of other metals, such as surgical steel, nitinol-based devices can be placed into remarkably smaller diameter catheters for a wide range of catheter-based procedures. However, a disadvantage associated with nitinol is that it remains in the circulatory system permanently (it is not biodegradable) and sometimes increases the risk of thrombosis, infections, and restenosis. Thus, an endovascular device in accordance with the invention constitute about 10% or less of nitinol, based on the total mass of the device.

Further, in accordance with the invention, at least a portion of the skeletal structure has deposited thereon or applied thereto a deposition material selected from biodegradable polymer, thin film nitinol and, mixtures and combinations thereof.

The biodegradable polymer includes, but is not limited to, polyester, polyurethane urea and, blends and combinations thereof, and constitutes about 10% or less of the total mass. The biodegradable polymer can be in the form of a coating or membrane that covers at least a portion of the biodegradable metal, due to their low profile feature and biocompatibility.

Commercially available polymeric biomaterials suitable for use in the invention include ePTFE, Dacron, polycaprolactone (PCL), poly-L-lactic acid (PLLA), polyglycolic acid (PGA) and, mixtures and combinations thereof. Some polymeric biomaterials, e.g., ePTFE and Dacron, are not degradable. Certain polyurethane ureas (PUUs) have been shown to possess good biocompatibility with non-toxic degradation products and high elasticity and strength, even in very thin (<1 mm) formats.

PUUs include soft segments (polycaprolactone, polyethylene glycol, polycarbonate, and the like), diisocyanatebutane and chain extender putrescine. In certain embodiments, PUU copolymer is prepared by a two-step polymerization process whereby polycaprolactone diol, 1,4-diisocyanatobutane, and diamine are combined in a 1:2:1 molar ratio. In the first step, a pre-polymer is formed by reacting polycaprolactone diol with 1,4-diisocyanatobutane. In the second step, the pre-polymer is reacted with diamine to extend the chain and to form the final polymer. The degradation profiles and mechanical properties can be tailored or pre-selected by changing the molecular weight and the composition of the soft segments. A thermoplastic elastomer is easy to process into various different shapes. Of specific interest to tissue engineering applications, porous scaffolds can be made from polyurethanes using fabricating processes, such as, thermally induced phase separation, salt leaching, and electrospinning.

In certain embodiments, the biodegradable polymer is deposited in the form of a coating on at least a portion of the frame structure, e.g., on the biodegradable metal segments. The coating can be in the form of electrospun fibers. PUU can be directly deposited onto the metallic frame by using various conventional apparatus and techniques known in the art, such as but not limited to, electrospinning. Electrospinning is a well-established method for producing polymeric micro- and nano-fibers, which includes utilizing electrostatic forces to uniaxially stretch a viscoelastic jet derived from a polymer solution or melt into fibers with small diameters, e.g., forming fibrous mats. The micro-morphology of the fibrous mats can be tailored by varying the polymer solution concentrations, the polymer molecular weight, the feed rate of the polymer solutions, the distance from the source to the target, the voltage between the source and the target, and the rotational speed of the collecting mandrel. The resulting electrospun fibrous mats made from PUU have the appearance of a white, nonwoven fabric.

Figure 2:
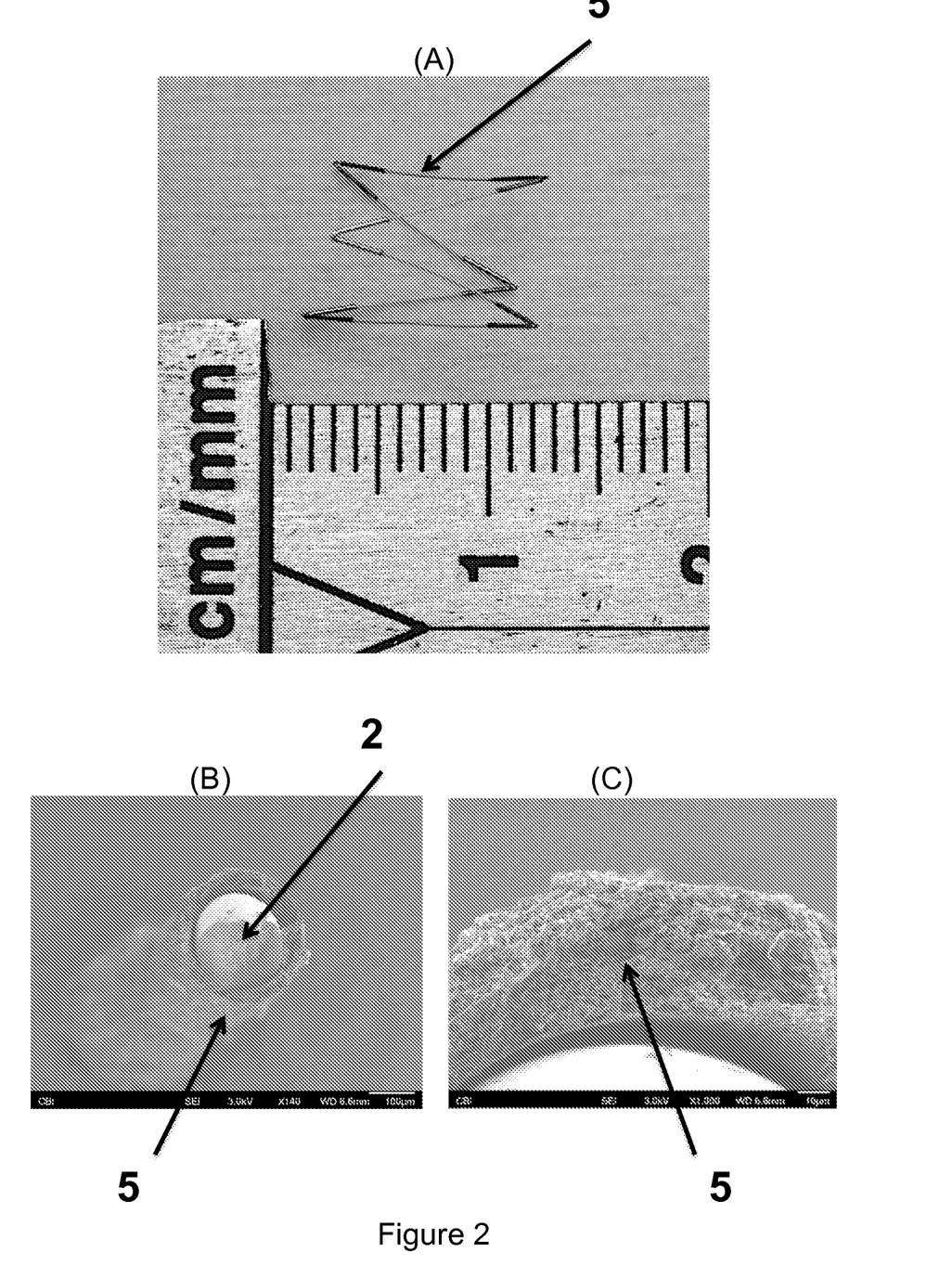
FIG. 2A is the image of FIG. 1A, further showing a biodegradable polymer coating formed on the biodegradable metal wires.
FIG. 2B is an image showing a detailed view of the biodegradable polymer coating, in the form of electrospun fibers, formed on the biodegradable metal wire as shown in FIG. 2A.
FIG. 2C is an image showing a detailed view of the electrospun fibers on the biodegradable metal wire as shown in FIG. 2B.

FIG. 2A shows the stent frame structure as shown in FIG. 1A and further includes a biodegradable coating 5 deposited on the biodegradable metal wires 2 (shown in FIG. 1A). FIG. 2B is a detailed view showing one of the metal wires 2 having deposited thereon the biodegradable coating 5, which includes electrospun fibers. FIG. 2C is a detailed view of the electrospun fibers that compose the biodegradable coating 5 (as shown in FIGS. 2A and 2B).

The thin film nitinol for use in the invention can include micro-patterned thin film nitinol, which is connected onto the skeletal structure or backbone, for example, by stitching with ultra-fine nitinol thread (e.g., about 22 µm thickness), such as for heart valve leaflets. The thin film nitinol can be fabricated using conventional processes and apparatus known in the art. In certain embodiments, suitable thin film nitinol for use in the invention is fabricated by a DC sputter deposition technique using a near equiatomic nitinol target under ultra-high vacuum atmosphere. "Hot-target" sputter deposition and micropatterning to create thin film nitinol with fenestrations can be conducted as follows. Photoresist is deposited on a (4-inch) silicon wafer in a desired or pre-selected micropattern. A deep reactive ion etching technique is used to create trenches (50 micrometers in depth) around the photoresist. The etching rate varies and can be approximately one minute for each one micrometer in depth.

After removing the photoresist layer, a sacrificial layer of copper followed by an inhibitory silicon dioxide layer are deposited. Then, the thin film nitinol is sputter deposited on sheets (6 micrometer in thickness) and removed from the silicon oxide layer. Following deposition and removal, the film is crystallized for (120 minutes at 500° C.) in a vacuum (of less than $1 \times 10^{-7}$ torr). The thin film nitinol material used in the invention can have an austenite finish temperature of about 34° C. The film can then undergo a final cleaning treatment consisting of sequential rinsing in acetone, methanol, and ethanol (for five minutes) prior to use.

As described herein, the superelastic material, e.g., nitinol, is used to form miniature connectors for joining biodegradable metal segments in the skeletal structure of an endovascular device, to allow the device to be deformed and then return to its original shape. In its deformed state, the collapsed skeletal structure is inserted into a delivery tube and then deployed at a vascular target site within the body of a patient. The delivery tube can include any tubing that mimics a blood vessel, such as, but not limited to, a delivery catheter. Further, the delivery tube can be composed of a variety of known materials for this purpose. In certain embodiments, the delivery tube is silicone tubing. Upon deployment, the skeletal structure returns to its original, e.g., expanded, state. The skeletal structure can be, for example, a stent and stent graft.

The deposition material, thin film nitinol and/or biodegradable polymer material, can be used as scaffolds for soft tissue development, such as valve leaflets. In certain embodiments, nitinol thread can be used to stitch thin film nitinol or PUU membrane onto the metallic frame for heart valve leaflets.

Figure 3:
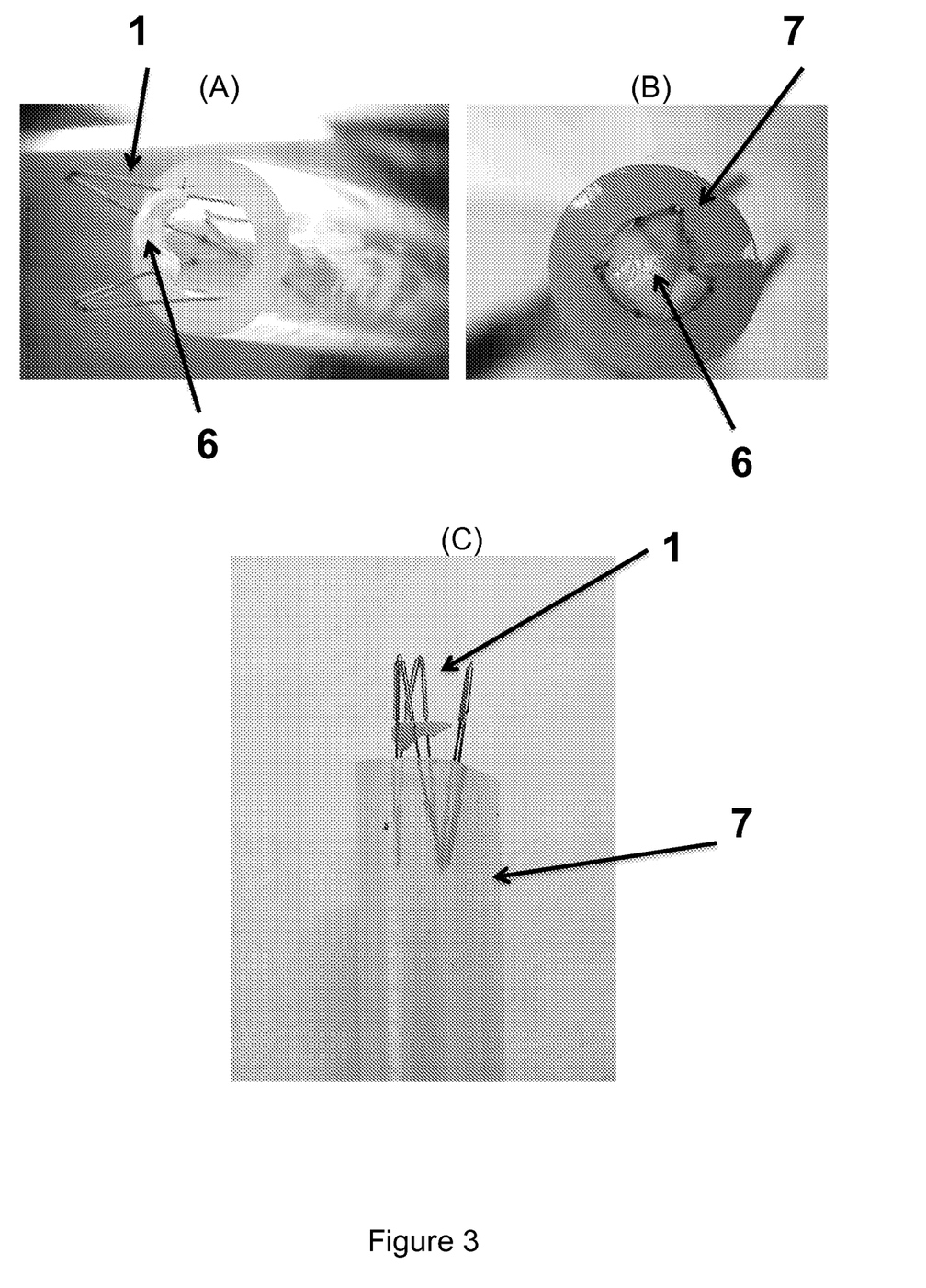
FIG. 3A is an image showing a stent frame structure, with a leaflet, collapsed in a silicone tube.
FIG. 3B is a top view of FIG. 3A.
FIG. 3C is a side view of FIG. 3A.

FIG. 3A is a front view showing a collapsed stent frame structure 1 and a single leaflet 6. A suture (not shown) is used to attach the leaflet on the backbone of the stent frame structure 1. The stent frame structure 1 is collapsed inside a delivery tube 7. FIG. 3B is a top view of the delivery tube 7 and the leaflet 6 contained therein, and FIG. 3C is a side view of the delivery tube 7 containing the collapsed stent frame structure 1 with the leaflet 6 attached thereto.

Figure 4:
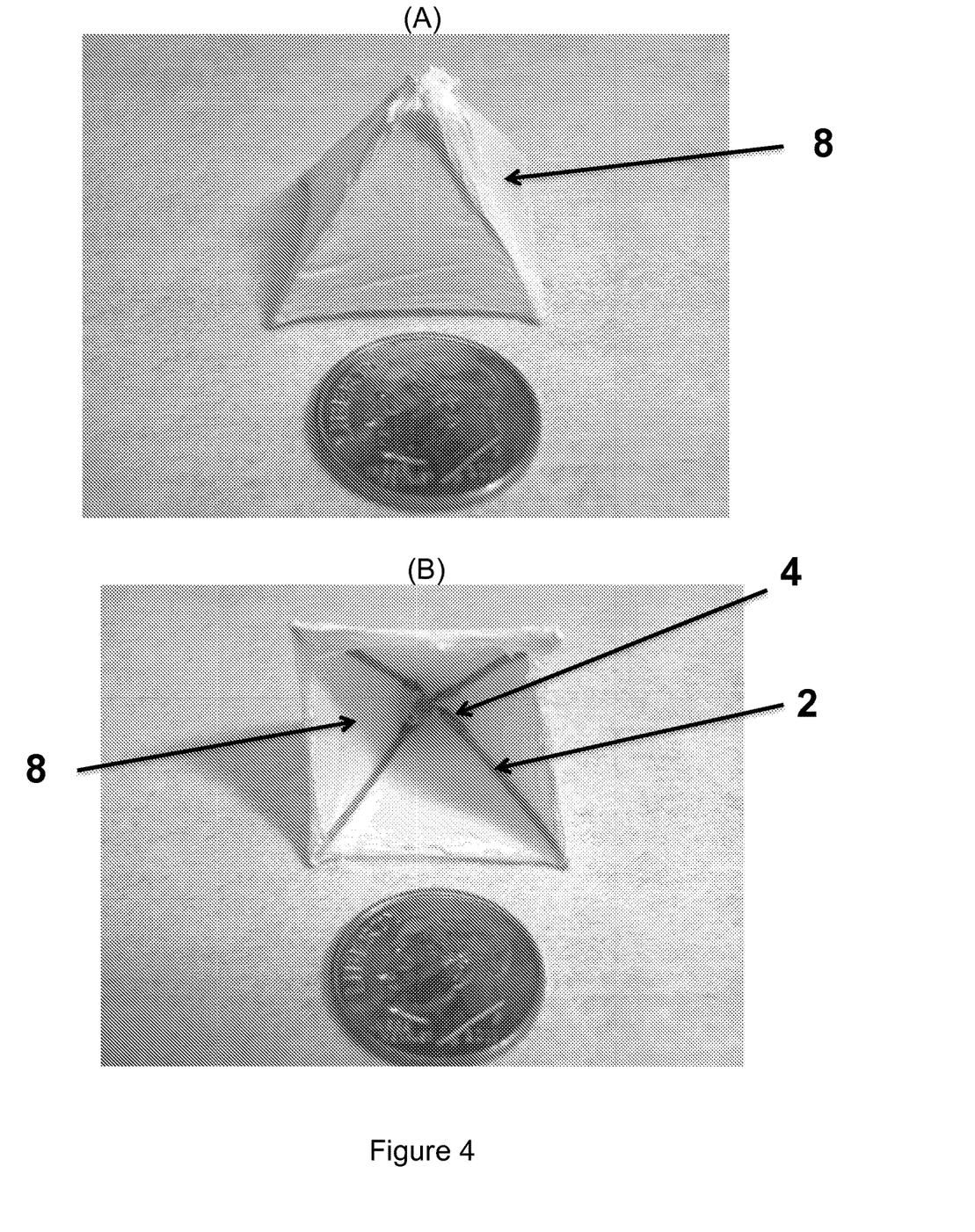
FIG. 4A is an image showing the outer surface of a vascular occlusion frame, composed of a biodegradable polymer membrane.
FIG. 4B is an image showing the inside surface of the vascular occlusion frame shown in FIG. 4A, including the biodegradable metal wires and superelastic material connector segments.

In certain embodiments of the invention, a vascular occlusion frame can be constructed using the biodegradable metal segments and the superelastic connector segments. In this embodiment, a biodegradable polymer membrane is deposited on or applied to the frame (in a pyramidal shape) to form an outer surface thereon. FIGS. 4A and 4B shown a vascular occlusion frame including a biodegradable polymer membrane 8. FIG. 4A shows the outer surface of the frame, which is composed of the biodegradable polymer membrane 8. FIG. 4B shows the inside surface of the frame, including the biodegradable metal wires 2 and the superelastic connecter tubes 4.

Figure 5:
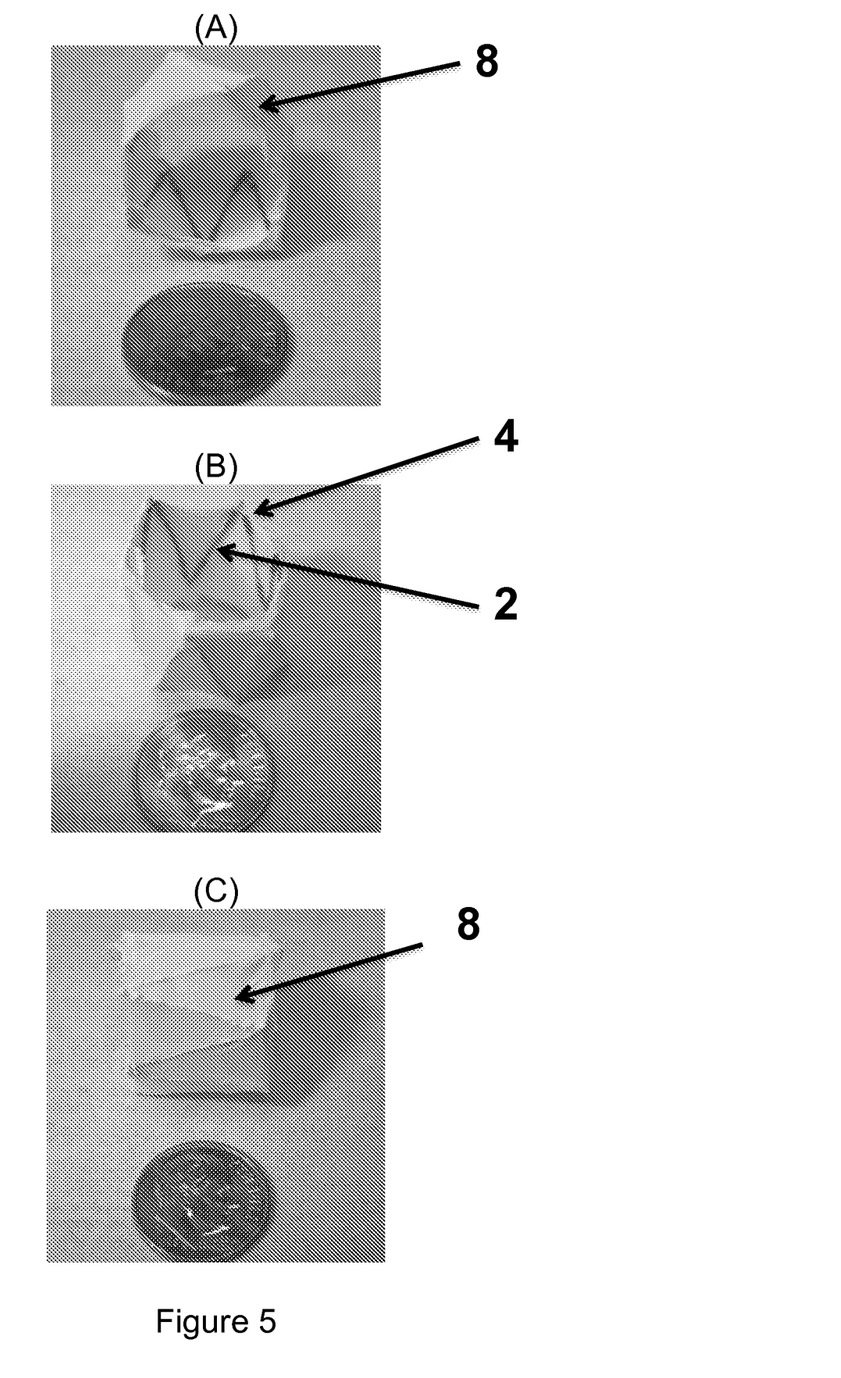
FIG. 5A is an image showing a stent graft frame, including a biodegradable polymer membrane applied to the backbone of the frame.
FIG. 5B is an image showing the inside surface of the stent graft frame shown in FIG. 5A, including the biodegradable metal wires and superelastic material connector segments.
FIG. 5C is an image showing the biodegradable polymer membrane outside surface of the stent graft frame shown in FIG. 5A.

FIGS. 5A, 5B and 5C show a stent graft frame, in accordance with certain embodiments of the invention. As shown in FIGS. 5A and 5C, there is the biodegradable polymer membrane 8 deposited on or attached to a backbone of the stent graft frame. FIG. 5B shows the inner surface of the stent graft frame, including the biodegradable metal wires 2 and the superelastic connector segments 4.

Figure 6:
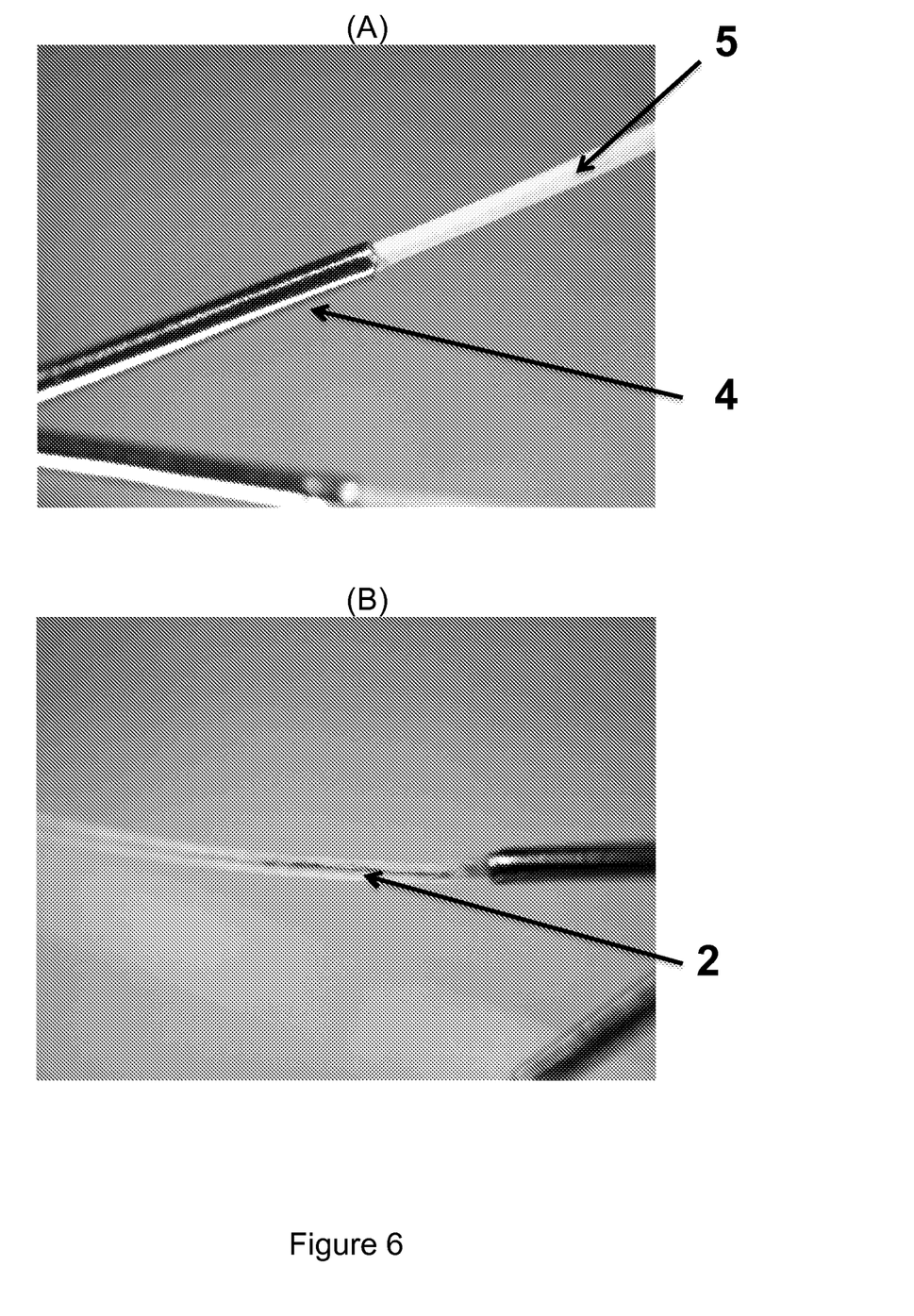
FIG. 6A is an image showing a biodegradable polymer coating (on a biodegradable metal wire as shown in FIG. 2A) and an integrated superelastic material connector (tube)
FIG. 6B is an image showing the presence of the biodegradable metal wire in the biodegradable polymer coating as a portion of the biodegradable metal wire degrades over a period of time.
Figure 7:
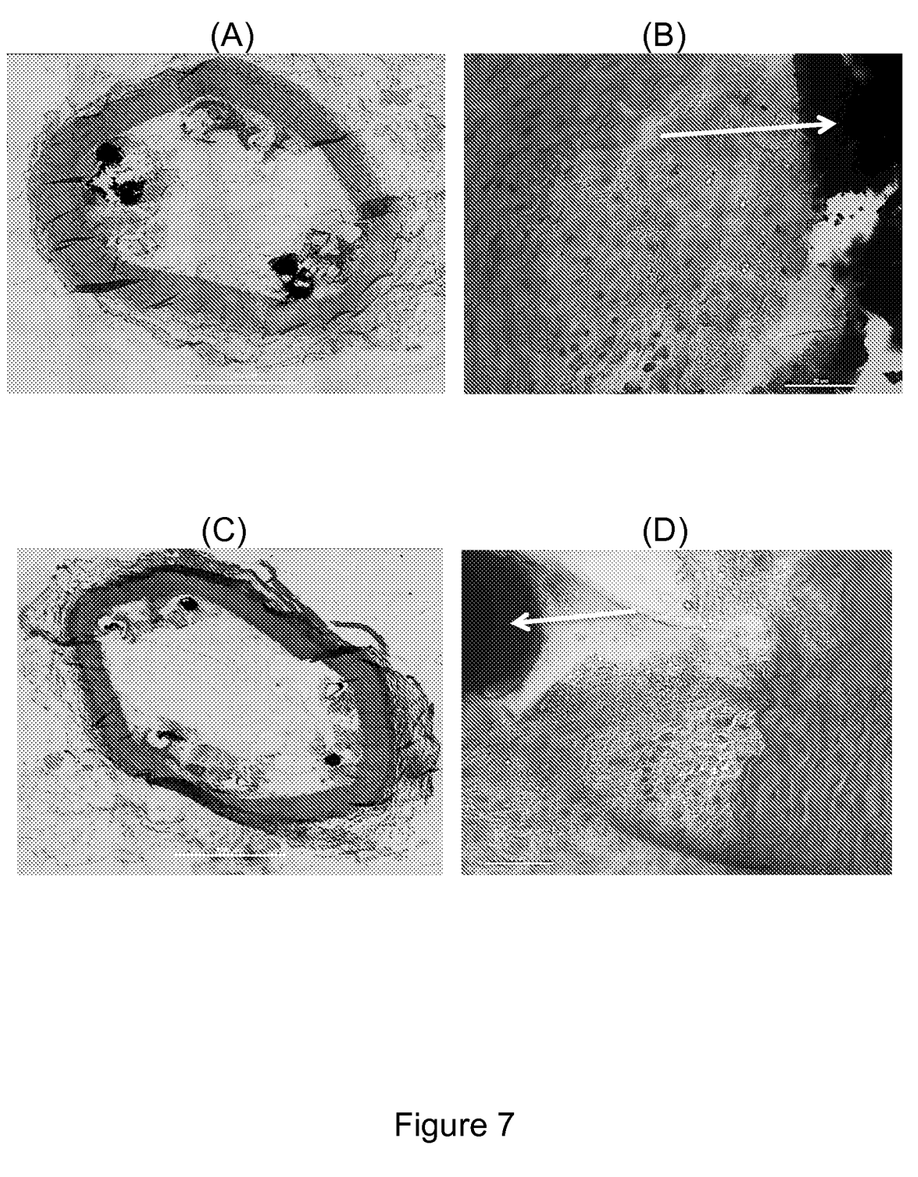
FIGS. 7A, 7B, 7C and 7D are images showing a stent structural framework that was implanted at a target location and the degradation of the biodegradable metal wire after one month.

Without intending to be bound by any particular theory, it is believed that the presence of a biodegradable polymer coating on a biodegradable metal wire increases its length of time for degradation. FIG. 6A shows the biodegradable polymer coated wire and superelastic tube as shown in FIGS. 2B and 2C, wherein the biodegradable wire 2 has deposited thereon the biodegradable polymer coating 5 that is composed of electrospun fibers. FIG. 6B shows that after a period of time a portion of the biodegradable metal wire 2 is degraded. The wire is degraded and the remaining electrospun fiber coating is effective to support the structure.

In certain embodiments, the endovascular devices of the invention are composed of a combination of nitinol, magnesium and polyurethane urea (PUU). Each of these materials, individually, is known in the art as a biomaterial for use in medical devices. For example, individually, nitinol is known for use in constructing self-expanding devices and, individually, magnesium is known for constructing biodegradable devices. These devices that contain nitinol only or magnesium only have been found to exhibit a lack of ductility However, in accordance with the invention, nitinol, magnesium and PUU are combined, e.g., integrated, to form endovascular devices that demonstrate self-expanding and bioabsorbable properties.

In accordance with the invention, endovascular devices are constructed of a combination, e.g., integration, of metal alloy (superelastic material), biodegradable metal and, biodegradable polymer and/or thin film nitinol. In certain embodiments, the endovascular devices include a combination of nitinol, magnesium (or magnesium alloy or iron or mixture thereof) and PUU or thin film nitinol. These devices are elastically deformable and collapsible to a small diameter, e.g., for catheter-based delivery, and deployable in conduits that serve the vasculature in vitro. Thus, these three materials can be integrated, collapsed, delivered and deployed. In certain embodiments, the endovascular devices include frames formed of straight pieces or segments composed of biodegradable metal (e.g., magnesium/magnesium alloy), which are connected by a superelastic material (e.g., nitinol) to form a skeletal structure that is covered with a polymer membrane (e.g., PUU) or thin film nitinol.

Benefits and advantages of endovascular devices composed of the integration of nitinol, magnesium and, PUU and/or thin film nitinol, as compared to conventional materials for use in constructing endovascular devices, include one or more of the following:

(i) gradual integration with tissue, e.g., tissue growth at the deployment site offsets the loss of mechanical properties with the degradation of magnesium;

(ii) ultra-low profile design since the fabrication process is ideally suited for highly tortuous cerebral arteries or weakened arteries;

(iii) ballooning is not required for the deployment of a stent, stent graft, and heart valve, which reduces potential blood vessel injuries and embolization of broken atherosclerotic plaque (e.g., for balloon angioplasty);

(iv) tailoring of mechanical properties;

(v) customization of the initial and final geometry; and (vi) minimal residue of the vascular devices (e.g., only nitinol connections will remain, less than 10% of the total mass of the endovascular device).

Optionally, the metal alloy, biodegradable metal and deposition material (biodegradable polymer and/or thin film nitinol) can be combined, e.g., integrated, with other materials, such as, but not limited to, glue, suturing materials, other metallic wires, and welding materials. In terms of geometry of the endovascular devices, they should be sufficiently low profile and conformally deployed without disrupting blood flow after the placement in the circulatory system. Metallic frame components, such as wires and strips, can be manufactured by either conventional or advanced manufacturing processes. For example, powder metallurgy or electroforming are used for producing magnesium wires or strips, and powder metallurgy, heat annealing, and, potentially, laser cutting processes are used for producing nitinol wires or strips. These conventional fabrication processes and the apparatus used therewith are commercially known.

In certain embodiments, the endovascular devices of the invention may be lubricated in the absence of glue, suturing materials, other metallic wires and welding materials. These embodiments include microscale mechanical clamping (or insertion) of nitinol and magnesium, and direct deposition of PUU and/or thin film nitinol onto a backbone metallic frame structure. In certain embodiments, nitinol and magnesium are connected by inserting magnesium wire into a nitinol tube and then, mechanically clamping or using a small amount of biocompatible polymer adhesive. For the micropatterned thin film nitinol or PUU membrane, an ultra-fine nitinol thread (i.e., 22 μm thick) can be used to connect the film or membrane onto the nitinol-magnesium metallic frame.

The fabricated endovascular device according to the invention can be integrated and deployed into a wide variety of systems to target a diverse set of medical conditions and diseases. For example, after the endovascular device has been fabricated, it can be successfully integrated into a stent delivery catheter system. In certain embodiments, the device is initially cooled to below 5° C., to allow the nitinol material to be easily deformed (i.e., converting to a malleable martensite phase in nitinol). Once the device is deformed into a collapsed geometry, the device is inserted into the delivery catheter. Deployment may be achieved through a pushrod passed through the delivery catheter. Standard off-the-shelf delivery systems can be used to deploy the devices in vivo and in vitro. Upon the device being deployed and exposed to the blood temperature (i.e. in-vitro and in-vivo), the device conformally deploys in the vascular lumen (i.e., converting to the fully recovered austenite phase in nitinol).

In accordance with the invention, the combination and integration of superelastic and biodegradable materials, e.g., components, allows a tissue engineering approach to be pursued where no permanent foreign body is left behind other than small nitinol pieces. FIGS. 7A, 7B, 7C and 7D show that a stent structural framework was implanted at a target location and after one month, the biodegradable iron wire had disappeared.

In some settings (e.g., esophagus) the remaining pieces may dislodge and be cleared by the body. In other instances (e.g., cardiac septum) the superelastic components, e.g., nitinol connectors, are encapsulated in the developing soft tissue. Thus, constrictive geometries that are not capable of growing with a child are avoided (e.g., in stents) and the risk of infection, fibrosis or abrasion from left behind structures are also minimized. Further, healing or new tissue growth may be achieved with these devices over a time period from weeks to months.

According to the invention, the integration of nitinol, magnesium and PUU can be employed to provide the following medical devices:

1) Cardiovascular/peripheral artery stents or stent grafts for vascular reconstruction or the treatment of diseased segments;

2) Ultra-low profile intracranial aneurysm stents;

3) An atrial septal defect (ASD) closure device for treating the heart wall defects;

4) An inferior vena cava (IVC) filter for treating venous thromboembolism;

5) Vascular plugs or occluders for temporarily treating hemorrhage or for embolic treatment in cancer;

6) Carotid artery stent grafts for isolating atherosclerotic plaque;

7) Esophageal healing stents to temporarily hold surfaces such as extracellular matrix based materials against the stripped esophageal wall; and 8) An ultra-low profile pediatric heart valve that may have the potential to grow with a child.

In general, the invention is applicable to adult and pediatric applications where a temporary need exists to provide scaffolding with mechanical support. The medical implant devices, e.g., endovascular devices, constructed and formed in accordance with the invention are effective to provide support acutely. These devices can include nitinol in an amount that constitutes about 10% or less of the total mass, and biodegradable material (that disappears over a specified period of time) in an amount that constitutes at least about 90%. Target applications or conditions include congenital patent ductus arteriosus, aortic arch repair for restenosis of post-coarctation, pulmonary artery (PA) stenosis in post-PA plasty or BT shunt stenosis in children, systemic venous stenosis (post Fontan operation).

EXAMPLES

Two different material stent graft groups, i.e., Group 1 and Group 2, were compared following implantation in abdominal aorta of rabbit. New Zealand White rabbits weighing about 3.5 kg were used. A midline abdominal incision was made to expose the infrarenal aorta. The aorta was clamped, an aortotomy was performed, and a catheter with stent inside was inserted into the aorta. The stent was then successfully deployed. No damage or expansion was observed on the aorta wall after stent deployment. In Group 1, the stent was a PUU monocusp, e.g., leaflet, with iron-nitinol frame. In Group 2, the stent was an iron-nitinol frame, without the leaflet. Group 2 served as a control to eliminate the effects of the valve, which may have thrombogenicity due to disturbed flow effects that are independent of the supporting stent structure. The in vivo studies had 1 week and 1 month endpoints for each group. At the 1 week endpoint, acute thrombogenicity and placement stability was evaluated. Gross examination of the artery showed no embolism and no signs of abnormalities. Neither migration nor collapse was observed for the stent. Histology studies showed that there was a small layer of membranous thrombus covering the stent struts. The interface between the aorta and the metallic struts showed accumulation of brownish iron debris and the luminal surface adjacent to the stent struts had a brownish tinge. Iron laden macrophages or lymphocytes, ranging from a sparse isolated localization to accumulation in clusters, were found close to the stent struts. At the 1 month endpoint, early remodeling characteristics of the monocusp valves and stent graft was evaluated. The iron stent struts were integrated into the artery wall, with both nitinol and iron parts covered completely with a neointima. Adjacent to the iron stent struts, there were accumulation of degradation products accompanied by macrophages.

Whereas particular embodiments of the invention have been described herein for purposes of illustration, it will be evident to those skilled in the art that numerous variations of the details may be made without departing from the invention as set forth in the appended claims.

What is claimed is:

1. An endovascular medical implant device, comprising:
   a structural frame, elastically deformable from an original structure to a collapsed structure, comprising:

a plurality of elongated straight segments composed of biodegradable metal wire, each of the plurality of elongated straight segments having a length extending between a first segment end and an opposite second segment end, wherein the biodegradable metal wire constitutes about 80% or greater of the total mass of the device;

a plurality of connectors each composed of nitinol, comprising a straight tube having an outer surface, an opening formed by the outer surface, a first tube end, a second tube end, and a length extending between the first and second tube ends;

a plurality of struts each composed of nitinol in a form selected from the group consisting of a v-shape wire and a u-shape wire, having a first strut end face and a second strut end face, wherein a total of the nitinol constitutes about 10% or less of the total mass of the device;

a biodegradable polymer in a form of a coating comprising electrospun fibers deposited on a surface of one or more of the plurality of elongated straight segments, wherein the biodegradable polymer constitutes about 10% or less of the total mass of the device, wherein one or more pairs of the plurality of elongated straight segments are connected together by the plurality of connectors and the plurality of struts to form the structural frame, wherein the first segment end of a first one of the plurality of elongated straight segments is connected to the first tube end of a first one of the plurality of connectors, and the first strut end face of a first one of the plurality of struts is connected to the second tube end of the first one of the plurality of connectors, and wherein the second strut end face of the first one of the plurality of struts is connected to the second tube end of a second one of the plurality of connectors, and the first segment end of a second one of the plurality of elongated straight segments is connected to inserted into the first tube end of the second one of the plurality of connectors.

2. The endovascular medical implant device of claim 1, wherein the biodegradable metal wire is composed of a metal selected from the group consisting of magnesium, iron and, alloys and mixtures thereof.

3. The endovascular medical implant device of claim 1, wherein the biodegradable polymer coating comprises a polymer selected from the group consisting of polyester, polyurethane urea, polycaprolactone, poly-L-lactic acid, polyglycolic acid and mixtures thereof.

4. The endovascular medical implant device of claim 1, wherein a sheet in a form selected from the group consisting of a polymer membrane, nitinol membrane, polymer thin film, and nitinol thin film is connected to a backbone of the structural frame to form an outer cover.

5. The endovascular medical implant device of claim 4, wherein the sheet is connected to the structural frame to form a valve leaflet.

6. The endovascular medical implant device of claim 4, wherein the biodegradable metal wire is composed of a metal selected from the group consisting of magnesium, iron and, alloys and mixtures thereof, and the sheet is polyurethane urea membrane.

7. The endovascular medical implant device of claim 1, wherein the collapsed structure is placed in a delivery tube, the collapsed structure is configured to be deployed from the delivery tube into a patient body and upon being deployed, the collapsed structure recovers the original structure.

8. The endovascular medical implant device of claim 7, wherein the delivery tube is a catheter.

* * * * *

UNITED STATES PATENT AND TRADEMARK OFFICE
CERTIFICATE OF CORRECTION

PATENT NO. : 10,888,442 B2
APPLICATION NO. : 15/525411
DATED : January 12, 2021
INVENTOR(S) : Youngjae Chun et al.

Page 1 of 1

It is certified that error appears in the above-identified patent and that said Letters Patent is hereby corrected as shown below:

In the Claims

In Column 16, Line 4, please delete: "inserted into"

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*